United States Patent [19]

Johnson et al.

[11] Patent Number: 5,673,473
[45] Date of Patent: Oct. 7, 1997

[54] METHOD OF SURFACE FINISHING A MEDICAL DEVICE SHIELD USING METALLIC MEDIA

[75] Inventors: Linda M. Johnson, Moundsview; Vyacheslav Mikhailov, Wayzata, both of Minn.

[73] Assignee: Medtronic, Inc., Minneapolis, Minn.

[21] Appl. No.: 351,988

[22] Filed: Dec. 8, 1994

Related U.S. Application Data

[63] Continuation-in-part of Ser. No. 83,735, Jun. 25, 1993, abandoned.

[51] Int. Cl.$^6$ .................................................. H01S 4/00
[52] U.S. Cl. .................. 29/592.1; 29/90.7; 29/527.7; 72/53; 148/325; 607/36
[58] Field of Search ................... 29/90.7, 90.5, 29/527.6, 527.7, DIG. 36, 422, DIG. 45, 592.1; 72/53, 42; 148/325, 516; 607/36; 451/296

[56] References Cited

U.S. PATENT DOCUMENTS

| | | | |
|---|---|---|---|
| 3,073,022 | 1/1963 | Bush et al. | |
| 3,734,837 | 5/1973 | Blair et al. | |
| 3,787,191 | 1/1974 | Duncan | 72/53 |
| 3,845,533 | 11/1974 | Tinfow | 29/90.7 |
| 3,974,673 | 8/1976 | Fosness | 72/348 |
| 4,077,811 | 3/1978 | Burman | 72/364 X |
| 4,250,726 | 2/1981 | Safian et al. | 72/53 X |
| 4,287,740 | 9/1981 | Kumar | 72/53 X |
| 4,356,717 | 11/1982 | Okunishi | |
| 4,474,044 | 10/1984 | Leistner | |
| 4,550,487 | 11/1985 | Hoshino et al. | 29/527.7 |
| 4,581,913 | 4/1986 | Reed | |
| 4,865,652 | 9/1989 | Megusar et al. | 29/527.6 X |
| 5,057,108 | 10/1991 | Shetty | 72/53 X |
| 5,113,681 | 5/1992 | Guesnon | 72/53 |
| 5,277,048 | 1/1994 | Lubas | 72/53 |
| 5,344,494 | 9/1994 | Davidson et al. | 451/39 X |
| 5,431,695 | 7/1995 | Wiklund et al. | 439/909 X |

*Primary Examiner*—Peter Vo
*Assistant Examiner*—Khan Nguyen
*Attorney, Agent, or Firm*—Thomas F. Wooods; Harold R. Patton

[57] ABSTRACT

A surface finishing process for medical device shields achieves a highly scratch-resistant satin finish prior to encapsulation of the medical device within the shield. The satin finish is achieved by bead blasting the metallic substrate material with stainless steel beads before forming the final shield. The disclosed process eliminates the necessity for surface finishing the shield surface of a completed medical device.

4 Claims, 4 Drawing Sheets

METHOD OF SURFACE FINISHING A MEDICAL DEVICE SHIELD USING METALLIC MEDIA

CROSS REFERENCE TO CO-PENDING APPLICATION

This application is a continuation-in-part of commonly assigned U.S. patent application Ser. No. 08/083,735, filed Jun. 25, 1993, entitled "Method of Surface Finishing A Medical Device Shield Using Metallic Media", abandoned.

BACKGROUND OF THE INVENTION

1. Field of the Invention

The present invention relates generally to implantable medical devices and, more particularly, to surface treatment processes applicable titanium metal sheet stock used in the manufacture of medical device shields.

2. Description of the Prior Art

It is generally known that the fatigue and corrosion resistance properties of various metal alloys used in the manufacture of implantable medical devices can be affected by different surface treatment processes. For instance, one such process includes the steps of mechanical grinding, sisal buffing or color buffing, electropolishing, and passivation. Another process described in U.S. Pat. No. 5,057,108 issued to Shetty et al. includes the steps of stainless steel shot blasting, glass bead blasting, electropolishing, and passivation. U.S. Pat. No. 5,113,681, issued to Guesnon et al., describes a process and apparatus for forming a sheet element with contoured surface from a plane titanium alloy sheet by hot deep drawing in a press.

Surface finishing and bead blasting of implantable medical device enclosures in particular, however, has traditionally been performed during the device enclosure manufacturing process subsequent to formation of the device enclosure itself. This is because suppliers of titanium have been unwilling to invest in additional specialized processing equipment necessary for bead blasting material in the small quantities generally required by implantable medical device manufacturers. Another reason that surface finishing of implantable medical device enclosures has traditionally been performed at the finished device level is to eliminate any scratches or blemishes that have marred the device enclosure at earlier points in the enclosure manufacturing process. Therefore, while the surface finishing processes employed in the manufacture of titanium implantable medical device enclosures have been generally successful in providing devices having scratch-free surfaces, it is desired to develop a material finishing process that maintains a blemish-free surface while eliminating the necessity for the post-forming finishing processes normally associated with manufacturing of implantable medical device enclosures.

By way of comparison, Guesnon et al., forms a single three dimensional component from a sheet of titanium and thereafter performs a series of finishing operations. In contrast, the present invention performs the process steps on a continuous roll of titanium sheet stock, prior to forming, eliminating the need for subsequent processing steps.

SUMMARY OF THE INVENTION

Generally, the present invention provides a process for surface finishing material, and in particular a coil of rolled titanium is employed in forming implantable medical device enclosures, wherein the scratch resistance of the material is greatly enhanced without compromising biocompatibility properties of the titanium.

More specifically, the process of the present invention enhances the scratch resistance of a titanium implant device shield by causing a cold-worked, satin-type finish to be formed on the titanium device shield as the result of bead blasting with stainless steel beads.

In one aspect of the invention, the initial use of stainless steel beads for the material and subsequent touch-up of finished device shields results in total elimination of any residual cosmetic defects. In another aspect of the invention, the step of pickling a formed device shield is eliminated in favor of pickling a coil of rolled titanium prior to stainless steel bead blasting, thereby increasing manufacturing throughput without sacrificing shield biocompatibility.

An advantage of the method of the present invention is that device shields produced from bead blasted material are scratch-resistant and have a more consistent cosmetic finish/appearance than shields which are bead blasted after final device assembly.

Another advantage of the method of the present invention is that shields produced from bead blasted material are more susceptible to accepting graphics with more readable characteristics.

A further advantage of the method of the present invention is that shield manufacturing is simplified by the elimination of conventionally used post forming processing steps including shield pickling, straight line finishing, and final shield inspection after the device shield has been sized and trimmed.

Yet another advantage of the method of the present invention is that production of scrap shields is reduced, as is the manufacturing cycle time for the medical device shields.

The invention, in one form thereof, provides a method of manufacturing an implantable medical device shield/enclosure having enhanced scratch-resistant properties. The preferred method includes several steps, including an initial step of providing a metal substrate in the form of a titanium sheet stock, which may take the form of a coil of rolled titanium sheet. The metal substrate has a generally smooth surface which, pursuant to another step of the invention, is bead blasted on one or both sides with stainless steel beads until a satin-like layer is formed on the metal substrate. The cold-worked layer has a textured surface which, according to a further step of the invention, is drawn to form a shield. In another embodiment, one aspect of the invention according to this form, the textured surface is further bead blasted with metallic media i.e., stainless steel beads subsequent to shield annealing, trimming, and welding processes.

DESCRIPTION OF THE PREFERRED EMBODIMENT

Figure 1:
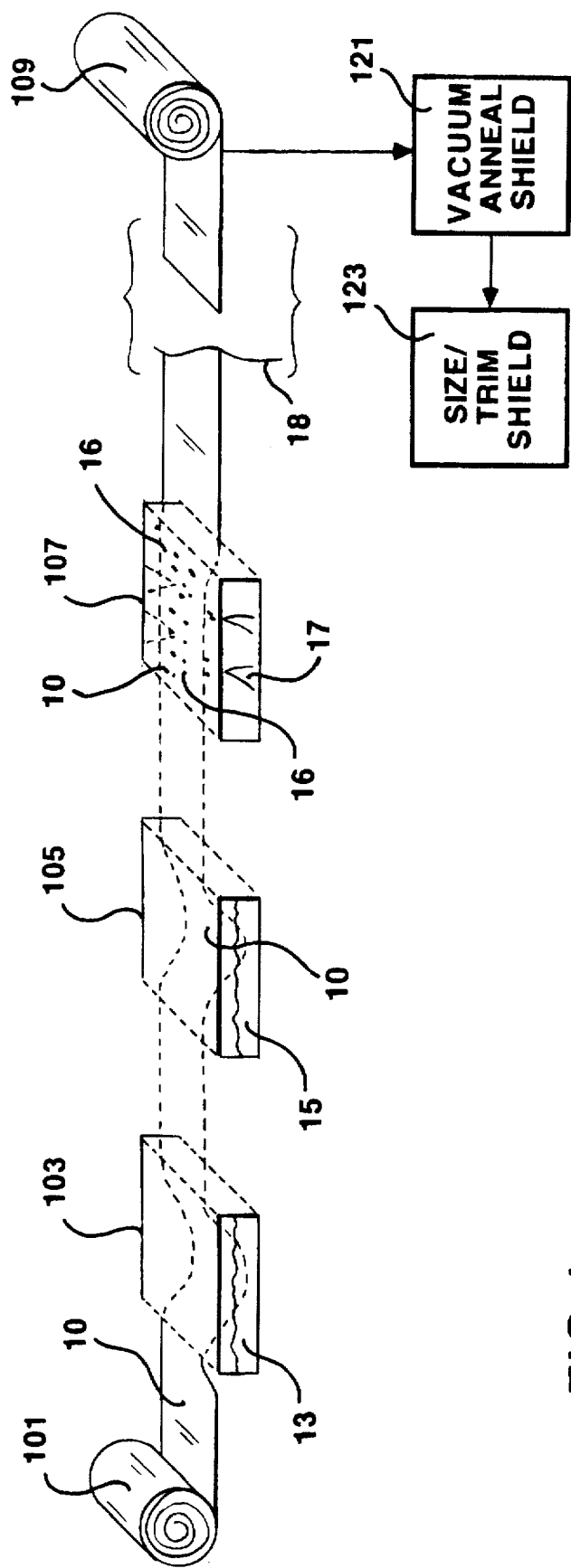
FIG. 1 is a diagrammatic representation of the process steps involved in an exemplary embodiment of the method of the present invention.

Referring now to FIG. 1, the steps for surface finishing titanium substrate 10 in accordance with an exemplary embodiment of the present invention are diagrammatically illustrated. Generally, 101 represents the first step of providing a coil of rolled titanium, which has been pre-rolled to a precise thickness of about 0.014". The titanium substrate material is used generally in the manufacture of implantable medical device shields due to its high strength, ductility, fracture resistance, biocompatibility, and corrosion resistance.

Turning now to the next step, block 103 depicts an alkaline rinse 13 prior to the pickling step 105. The rinsing step removes organic contaminates which reside on the surface of the titanium 10.

Block 105 represents the next step of pickling the titanium sheet 10 in an acidic solution 15 in accordance with conventional methods. The pickling process removes the oxide layer formed during the annealing step, not shown, and also cleans the substrate surface without dissolving away the surface layer produced during the rolling step 101.

Block 107 represents the next step of bead blasting 17 the pickled titanium substrate 10 with metallic media 16, preferably stainless steel beads. This step involves blasting the titanium substrate with stainless steel beads of a uniform size. In one embodiment, the stainless steel beads are selected to have a diameter of 0.002"–0.004" in diameter. Bead blasting with the stainless steel beads as hereinbefore described leaves a surface finish which has a satin appearance to the human eye. It is noteworthy that the combination of the titanium substrate and the 0.002"–0.004" diameter stainless steel beads leaves no stainless steel beads embedded in the titanium substrate subsequent to the bead blasting step 107.

Figure 3:
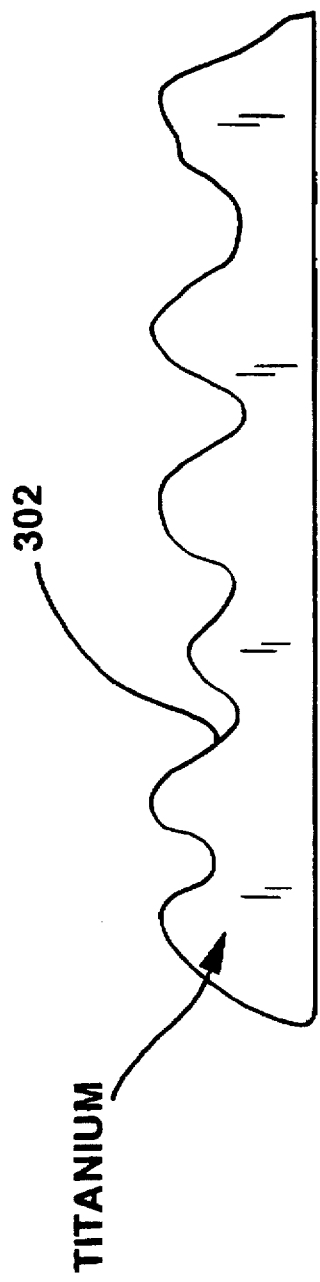
FIG. 3 is a pictorial view illustrating effects of bead blasting titanium with stainless steel beads.

FIG. 3 depicts a microscopic view of what a portion of the titanium substrate surface appears like following the bead blasting step 107. The substrate surface 302, although having significant indentations, remains free of any stainless steel beads.

Subsequent to the bead blasting step 107 the titanium substrate 10, which has been processed, is cut from the coil of rolled titanium 101 and is recoiled, hence a finished roll of titanium 109 is ready to be formed into medical device shields.

Figure 2:
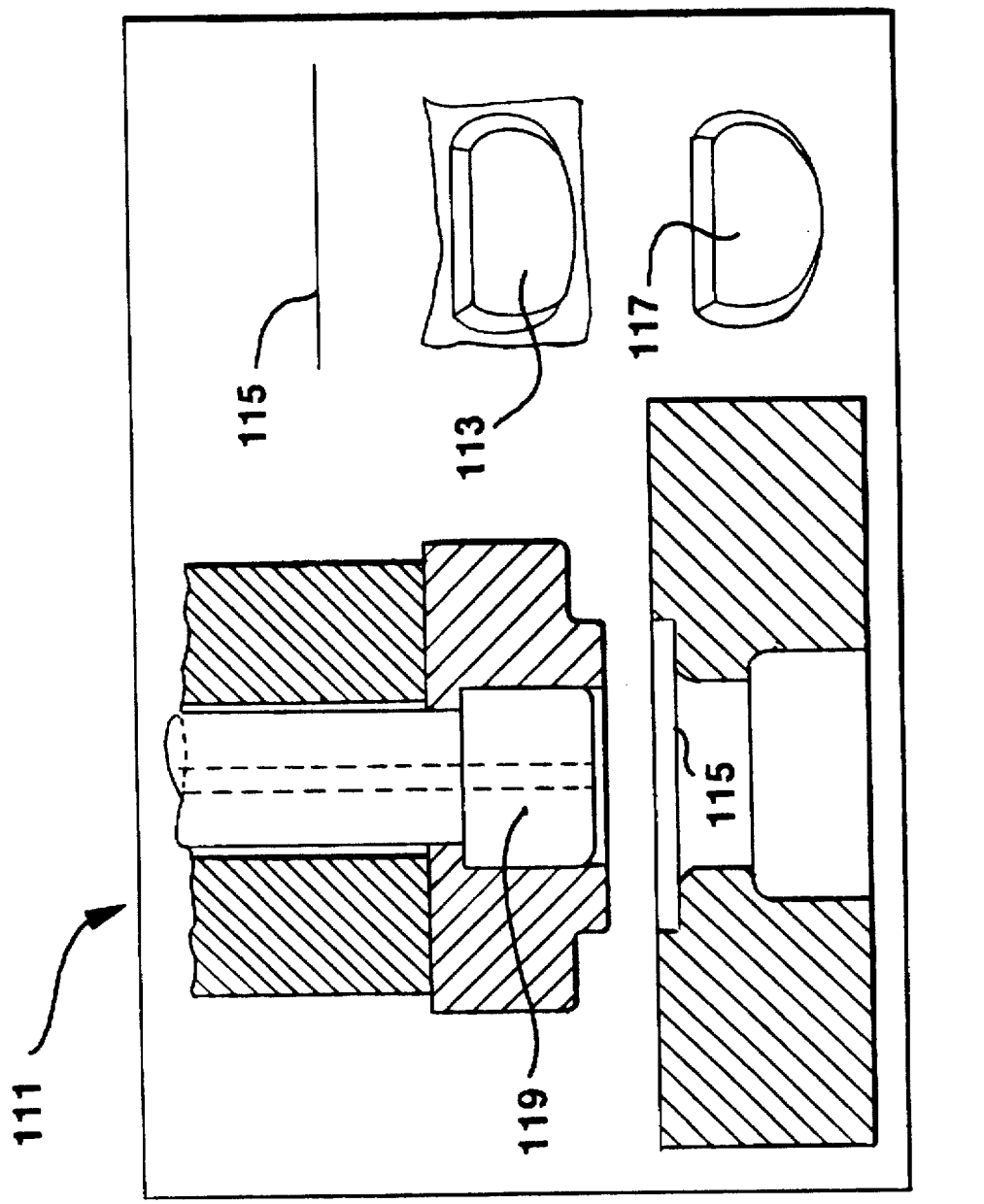
FIG. 2 illustrates a conventional drawing and forming apparatus and a view of a medical device shield half, manufactured in accordance with the method of the present invention.

Turning now to FIG. 2, the step of drawing and forming the device shield is performed in accordance with conventional methods 111 in FIG. 2. One embodiment of a device shield 117 is formed by a drawing and forming press 111 by first starting with a blank of processed titanium 115, cut from a coil of titanium sheet, processed as described above. Next, the drawing punch 119 forces the blank holder through the cylindrical opening in the die. In this way, a half shield is formed from the flat blank 115, as indicated by 115, 113, and 117, which show the blank 115, the half-drawn shield 113, and a finished device shield 117 after trimming for use as an enclosure for a cardiac pacemaker.

Because shield 117 has been drawn and formed from substrate material which has already undergone pickling 105 and bead blasting 107, it is no longer necessary to perform these same process steps on the completed device shield. However, overall cosmetic appearance on a completed medical device shield may occasionally be improved by performing a subsequent touch-up bead blasting step, preferably with metallic media i.e., stainless steel beads.

Figure 4:
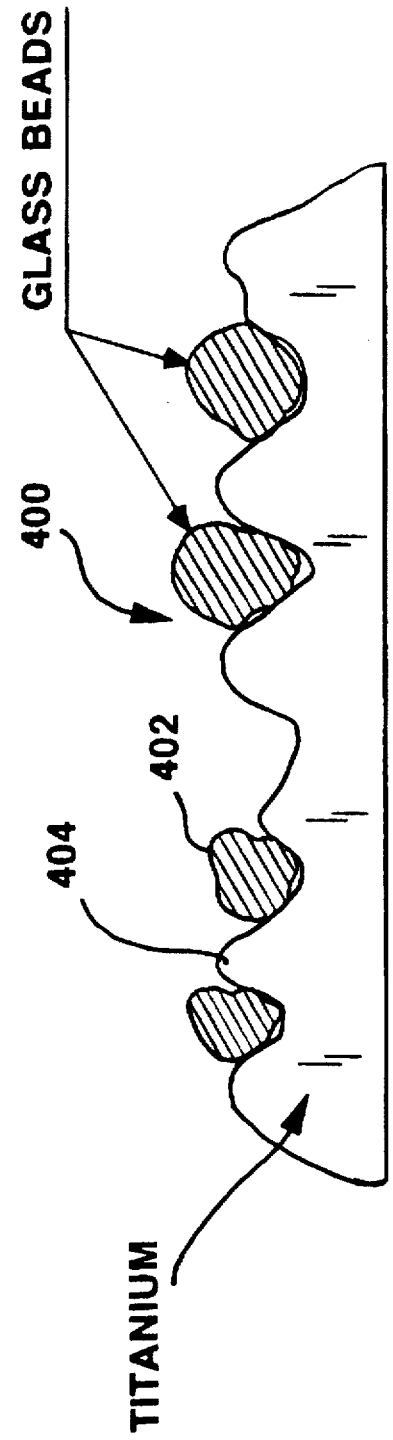
FIG. 4 is a pictorial view illustrating effects of conventional glass bead blasting of a finished device shield half where the device shield half is drawn and formed from the processed titanium shown in FIG. 3.

In contrast, FIG. 4 illustrates a drawn and formed device shield half 404 which has been bead blasted with glass beads 402 having a diameter of 0.004", a more conventional process known in the art. Glass bead residue 402 sits on the surface and does not react with the titanium. Because the glass beads 402 are not chemically bonded to titanium, they can be removed. In a subsequent parylene coating process, not shown, the parylene bonds with the glass residue 402. A boiling process, also not shown, breaks the glass-titanium bond wherein the parylene coating falls off removing the glass residue 402 from the titanium in the process. The glass bead touch-up processing hereinbefore described is not considered to be novel and is included to illustrate dissimilarities (as well as advantages of the inventive process) between the preferred bead blasting of a titanium substrate using stainless steel beads, and conventional bead blasting of a titanium substrate using glass/ceramic beads.

Moving now to step 121 in FIG. 1, the shield half is vacuum annealed in accordance with conventional methods. This step toughens the drawn and formed shield half by softening the titanium substrate thereby reducing its characteristic brittleness. It is necessary that bead blasting 107 with stainless steel beads be performed prior to vacuum annealing 121. Bead blasting 107 with stainless steel beads before the annealing step 121 will provide the desired results, i.e., preferred satin appearance, and substrate free of stainless steel residue from stainless steel beads.

The final step in the inventive process includes sizing and trimming 123 the shield half 113. Again, this step 123 is performed in accordance with conventional methods. Generally, the sizing and trimming step 123 is the final process step which takes place on the medical device shield prior to manufacture and encasement of the medical device itself within the device shield 117. Sizing and trimming 123 affects subsequent medical device manufacturing processes not shown, e.g., machining and welding operations. For example, accurate sizing and trimming 123 contributes to elimination of touch-up bead blasting discussed hereinbefore.

In one preferred embodiment of carrying out the process of the present invention, air pressure at about 25–30 psi is used with the stainless steel bead blasting apparatus to propel the stainless steel beads. All bead blasting is executed perpendicularly to the substrate/shield surface, i.e., an angle of incidence of 90, at a distance of about 4–6 inches from the tip of the nozzle. The time duration for bead blasting with stainless steel beads to achieve desired results for the target area varies according to several variables, including the hardness and density of the beads, and the velocity, flow rate, and angle of impact. However, for one exemplary bead blasting set-up, the desired satin surface finish is achieved with a process covering approximately 4 square feet/minute over the selected area.

Figure 5:
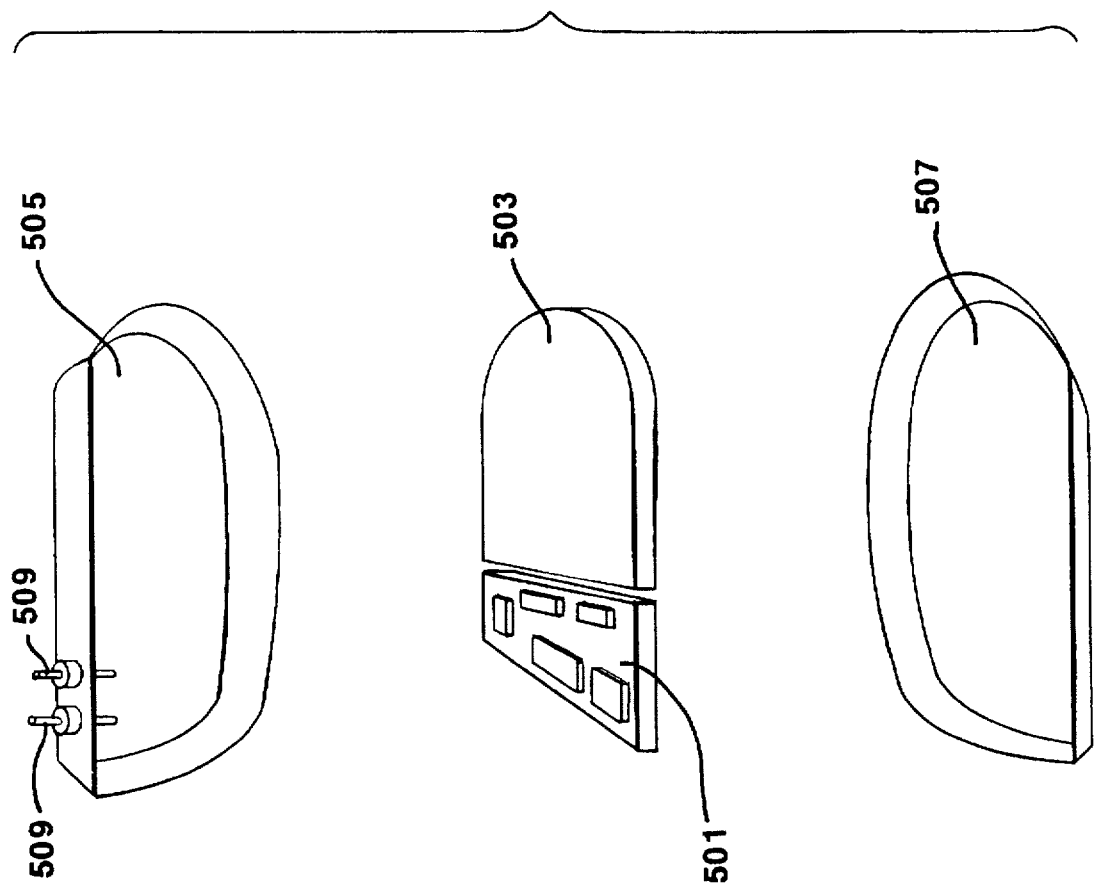
FIG. 5 is an exploded perspective view of the implantable medical device and the electronics which are hermetically sealed by the formed device shields.

Turning to FIG. 5, a finished medical device (e.g. a cardiac pacemaker) is formed by mounting one or more feed throughs 509 to one or more of the shield halves 505 and 507, enclosing the internal electronics 501 (e.g. pulse generator circuitry) and the battery cell 503 within the shield halves 505 and 507, coupling the battery 503 to the circuitry, coupling the circuitry to the feedthroughs 509 and subsequently laser welding the shield halves together along their edges to form a substantially hermetic enclosure. A molded plastic connector block assembly (not illustrated) containing electrical connectors for attachment to the feed throughs 509 is typically installed thereafter.

While the invention has been described above in connection with the particular embodiments and examples, one skilled in the art will appreciate that the invention is not necessarily so limited. For example, while as illustrated, both shield halves 505 and 507 are illustrated as three dimensional, formed components, an enclosure may be produced using only one three-dimensional, formed shield half and one planar, unformed shield half. It will thus be understood that numerous other embodiments, examples, uses, modifications of, and departures from the teachings disclosed may be made, without departing from the scope of the present invention as claimed herein.

What is claimed is:

1. A method of manufacturing an implantable electronic device, comprising the steps of:

providing a sheet metal substrate;

pickling said sheet metal substrate;

bead blasting said sheet metal substrate;

after said pickling and bead blasting steps, forming said bead blasted metal substrate to construct a three dimensional shield portion;

repeating the steps of providing, pickling, bead blasting and forming to construct an additional three dimensional shield portion;

locating an electronic circuit within said three-dimensional shield portion; and joining said three dimensional shield portion and said additional shield portion to one another to form a hermetic enclosure containing said electronic circuit.

2. The method according to claim 1 wherein said metal substrate is titanium.

3. The method according to claim 1 further comprising vacuum annealing said shield portion.

4. The method according to claim 3 further comprising sizing and trimming said vacuum annealed shield portion.

* * * * *